United States Patent
Herry et al.

(10) Patent No.: US 9,492,397 B2
(45) Date of Patent: Nov. 15, 2016

(54) ALCOHOL-RESISTANT SUSTAINED-RELEASE ORAL PHARMACEUTICAL FORM BASED ON MICROGRANULES

(75) Inventors: Catherine Herry, Saint-Ouen-du-Tilleul (FR); Laury Trichard-Trolet, Point de L'Arche (FR)

(73) Assignee: ETHYPHARM, Saint-Cloud (FR)

( * ) Notice: Subject to any disclaimer, the term of this patent is extended or adjusted under 35 U.S.C. 154(b) by 0 days.

(21) Appl. No.: 13/122,261

(22) PCT Filed: Oct. 2, 2009

(86) PCT No.: PCT/EP2009/062836
§ 371 (c)(1),
(2), (4) Date: Apr. 1, 2011

(87) PCT Pub. No.: WO2010/037854
PCT Pub. Date: Apr. 8, 2010

(65) Prior Publication Data
US 2011/0177138 A1    Jul. 21, 2011

(30) Foreign Application Priority Data
Oct. 2, 2008 (FR) ..................................... 08 56660

(51) Int. Cl.
*A61K 9/50* (2006.01)
(52) U.S. Cl.
CPC ........... *A61K 9/5078* (2013.01); *A61K 9/5026* (2013.01); *A61K 9/5036* (2013.01)

(58) Field of Classification Search
CPC ................ A61K 9/5078; A61K 9/5036; A61K 9/5026
See application file for complete search history.

(56) References Cited

U.S. PATENT DOCUMENTS

| | | | |
|---|---|---|---|
| 6,143,037 A * | 11/2000 | Goldstein et al. | 424/422 |
| 2002/0096235 A1 * | 7/2002 | Blomquist | 149/46 |
| 2006/0105039 A1 | 5/2006 | Lai et al. | |

(Continued)

FOREIGN PATENT DOCUMENTS

| WO | WO 02/065834 A2 | 8/2002 |
|---|---|---|
| WO | WO 02/096392 A1 | 12/2002 |

(Continued)

OTHER PUBLICATIONS

Cordova et al, Red Wine Protects the Heart, 2005, Science Daily, pp. 1-2, http://www.sciencedaily.com/releases/2005/03/050325222705.htm, last accessed Sep. 17, 2012.*

(Continued)

*Primary Examiner* — Trevor Love
(74) *Attorney, Agent, or Firm* — RatnerPrestia (57) ABSTRACT

Oral pharmaceutical form containing microgranules for the sustained release of at least one active principle, including a neutral carrier that is insoluble in water or in an alcohol solution, or a neutral carrier rendered insoluble in water or an alcohol solution, comprising at least one first mounting layer containing at least one active principle and optionally a pharmaceutically acceptable binding agent, wherein the whole comprises at least one coating based on at least one hydrophobic polymer.

9 Claims, 6 Drawing Sheets

(56) References Cited

U.S. PATENT DOCUMENTS

| | | |
|---|---|---|
| 2006/0165809 A1 | 7/2006 | Guimberteau et al. |
| 2007/0065512 A1 | 3/2007 | Dedhiya et al. |
| 2007/0092568 A1 | 4/2007 | Gore et al. |
| 2007/0196491 A1 | 8/2007 | Venkatesh |
| 2008/0003286 A1 | 1/2008 | Vemula et al. |
| 2008/0233197 A1 | 9/2008 | Matthews et al. |

FOREIGN PATENT DOCUMENTS

| | | |
|---|---|---|
| WO | WO 2007/093642 A2 | 8/2003 |
| WO | WO 2004/010983 A2 | 2/2004 |
| WO | WO 2006/047493 A2 | 5/2006 |
| WO | WO 2007/093642 A2 | 8/2007 |
| WO | WO 2007/109357 A2 | 9/2007 |

OTHER PUBLICATIONS

Walden et al., *The Effect of Ethanol on the Release of Opioids from Oral Prolonged-Release Preparations*, 33 Drug Development and Industrial Pharmacy 1101-1111 (2007).

International Search Report dated Oct. 27, 2010, issued by the European Patent Office in corresponding International Patent Application No. PCT/EP2009/062836.

* cited by examiner

ALCOHOL-RESISTANT SUSTAINED-RELEASE ORAL PHARMACEUTICAL FORM BASED ON MICROGRANULES

CROSS-REFERENCE TO RELATED APPLICATIONS

This application claims priority under 35 U.S.C. §119 to French Patent Application FR 0856660, filed on Oct. 2, 2008, and is a national phase of International Patent Application PCT/EP2009/062836, filed on Oct. 2, 2009, and designating the United States (published in the French language on Apr. 8, 2010, as WO 2010/037854 A2; the title and abstract were also published in English), each hereby expressly incorporated by reference herein in its entirety for all purposes and each assigned to the assignee hereof.

The invention relates to the use of an oral pharmaceutical form containing microgranules for the sustained release of at least one active principle, wherein said form is resistant to the immediate release of the dose of active principle in the presence of alcohol.

Many sustained-release pharmaceutical forms for oral administration exist on the market. Release of the active principle must be controlled according to the therapeutic objective and the pharmacological properties of the active principle. Certain active principles can prove to be highly toxic, even deadly, if the ingested dose exceeds a certain threshold.

It is thus imperative that their "delay" properties are tightly controlled in order to ensure that rapid release of the active principle, so-called dose dumping, cannot occur, in particular during the concomitant consumption of alcohol. The consumption of a great quantity of alcohol at the same time that a drug is taken can indeed alter the pharmaceutical form which then very rapidly releases the totality of the active principle contained therein.

PCT application WO 9611675 describes modified-release microcapsules for administration per os of medicinal and/or nutritional active principles, which size is less than or equal to 1000 µm. These microcapsules consist of particles covered by a coating material constituted a mixture of a film-forming polymer (ethylcellulose), a hydrophobic plasticizer (castor oil), a surfactant or lubricant (magnesium stearate) and a nitrogenous polymer (polyvinylpyrrolidone: povidone, PVP). These microcapsules are also characterized by their ability to remain for an extended period (at least 5 h) in the small intestine and to enable, during this time, the absorption of active principle over a period longer than that of natural transit in the small intestine.

PCT application WO 2007093642 describes a multiparticulate oral pharmaceutical form with an average diameter smaller than 2000 µm, constituted of at least one hydrophilic polymer, a core comprising the active principle and covered by a coating comprising at least one polymer insoluble in the liquids of the digestive tract, at least one plasticizer and optionally at least one surfactant.

In order to evaluate the alcohol resistance of pharmaceutical compositions, the FDA (United States Food and Drug Administration) suggests performing in vitro dissolution tests to compare the kinetics obtained in 0.1 N HCl medium (representative of gastric pH) with the kinetics obtained in the same medium substituted with 5%, 20% and 40% (v/v) ethanol. According to Walden et al. (The Effect of Ethanol on the Release of Opioids from Oral Prolonged-Release Preparations, Drug Development and Industrial Pharmacy, 33: 10, 1101-1111, 2007), the fact of exposing in vitro a pharmaceutical form over a period of 2 h is regarded as representative of the exposure time of these pharmaceutical forms in vivo.

An essential objective of the present invention is to provide a pharmaceutical form containing microgranules for the sustained release of at least one active principle for oral administration, making it possible to prevent or limit an immediate release of the active principle induced by the consumption of alcohol during the administration of said pharmaceutical form.

Definitions in the context of the present description of the invention:

Neutral Carrier

The term "neutral carrier" or "neutral core" or more simply "neutral" means spherical or quasi-spherical inert carriers of a size between 50 µm and 3 mm, preferentially between 100 µm and 1000 µm, such as those generally used in the pharmaceutical industry as a carrier base for active principles for the production of microgranules, for example.

Neutral Carrier Rendered Insoluble

A "neutral carrier rendered insoluble in water or in an alcohol solution" means a neutral carrier composed of materials that are soluble in water or in an alcohol solution covered with at least one layer of materials that are insoluble in water or in an alcohol solution and which function is to limit or to prevent the penetration of said media toward the core of the carrier.

Microgranules

The microgranules of the present invention relate to spherical galenic units, comprised in their center of a neutral carrier, covered with at least one layer containing the active principle which itself is covered with at least one polymer layer.

Sustained Release

In the present application, the term "sustained release" will be used to indicate a release profile of the active principle that is modified compared to that which the active principle alone would have had in an immediate release system as defined by the European Pharmacopoeia (quantity of active principle released in 45 minutes at least equal to 75%, Ph. Eur., 6th edition 2.9.3.)

Alcohol

The term "alcohol" refers to ethanol and the terms "alcohol solution" and "alcohol medium" refer to an aqueous ethanol solution.

The goal of the present invention is to provide a novel oral pharmaceutical composition containing microgranules constituted of three distinct parts. These microgranules are thus constituted, from the center toward the periphery, by at least one neutral carrier that is insoluble in water, then by at least one active layer comprising the active principles and finally at least one layer comprising at least one polymer of interest, that is to say, one polymer which properties are sought to be exploited in order to influence the release profile of the active principle.

In the prior art, for example in document WO 2007093642, the microparticles that enable the sustained release of the active principle in an alcohol solution generally constituted of a core of active principle that can be crude (pure) active principle in powder form, and/or a matrix granule of active principle mixed with various other ingredients, and/or a neutral carrier, for example of cellulose or of sugar, covered with at least one layer comprising the active principle. However, this document provides for the systematic incorporation of a pharmaceutically acceptable compound which speed or capacity to hydrate or to solvate is higher in an alcohol-free aqueous medium than in an alcohol solution (agent D), in various ways (in the core of the active principle, in the coating of the microparticles and/or the binder phase of the granules). However, Example 3 of the present invention shows that the incorporation of an agent D in the formulation of microgranules according to proportions claimed in document WO 2007093642 can lead to the loss of the sustained release effect in an alcohol-free medium. The incorporation of an agent D can thus be a major disadvantage in the formulation of alcohol-resistant sustained-release microgranules.

Moreover, document WO 2007093642 does not teach that the use of a water-insoluble neutral in the presence of a polymer coating comprised only of a hydrophobic polymer is suited to the sustained release of active principle in an alcohol solution.

This is why the technical problem that the invention proposes to solve relates to the use of a pharmaceutical form based on sustained-release alcohol-resistant microgranules comprising a neutral constituted of materials that are insoluble in water or in an alcohol solution or a neutral rendered insoluble in water or in an alcohol solution in the presence of a polymer coating with a delaying effect.

DETAILED DESCRIPTION OF THE INVENTION

The oral pharmaceutical form according to the invention comprises microgranules for the sustained release of at least one active principle, wherein each microgranule comprises a neutral carrier that is insoluble in water or in an alcohol solution or a neutral rendered insoluble in water or in an alcohol solution, comprising at least one first mounting layer comprising at least one active principle and optionally a pharmaceutically acceptable binder, the whole comprising at least one coating containing at least one hydrophobic polymer. The hydrophobic polymer prevents the immediate release of the active principle. Optionally, the inventive pharmaceutical form comprises at least one plasticizer preferably in the coating layer and optionally at least one surfactant preferably in the mounting layer.

The inventive oral pharmaceutical form is preferentially resistant to the immediate release of the dose of active principle to alcohol, and is characterized in that the percentage of active principle released after 2 h in an acid-alcohol medium of 0.1 N HCl containing alcohol and preferably a quantity of ethanol between 4% and 30%, is not more than 15 points (15% in absolute value) greater than that released in an acid medium of 0.1 N HCl.

Advantageously, the neutral carrier that is insoluble in water or in an alcohol solution comprises at least one hydrophobic excipient selected from cellulose, cellulose derivatives (microcrystalline cellulose), phosphate derivatives (calcium phosphates), silica and silicate derivatives (magnesium silicate, aluminum silicates and mixtures thereof).

Also advantageously, the neutral carrier rendered insoluble is obtained by covering a neutral at least partly with hydrophobic excipients selected from cellulose, cellulose derivatives (microcrystalline cellulose), phosphate derivatives (calcium phosphates), silica and silicate derivatives (magnesium silicate, aluminum silicates and mixtures thereof), titanium dioxide, waxes (microcrystalline wax, plant or animal waxes), shellac, polyvinyl acetate and/or phthalate, and lactic and glycolic acid polymers.

Preferably, the active principles are integrated in the active layer in combination with a pharmaceutically acceptable binder, such as those generally used in the pharmaceutical industry to attach active principles on the surface of neutral carriers. Thus, the method for attaching the active layer described in patent EP 1 200 071 can certainly be employed to attach the active layer in the context of the present invention.

Preferably, the active layer of the inventive microgranules is applied by the spraying of a dispersion of active principle in a solvent (called the mounting dispersion). Advantageously, this dispersion also contains the binder.

Among pharmaceutically acceptable binders, those used in the invention are preferentially hydrophilic binders and in particular cellulose derivatives such as HPMC, in particular Pharmacoat® 603 and Pharmacoat® 606 grades, polyvinylpyrrolidone derivatives, in particular PVP K-30 grade and also polyethylene glycol derivatives, in particular polyethylene glycol with a molecular weight between 3000 and 7000, such as PEG4000 and PEG6000 in particular, and mixtures thereof.

The solvent of the sprayed mounting dispersion must be suited to the active principle or mixture of active principles employed. Thus, water or organic solvents, including ethanol or hydroalcoholic solutions of various concentrations, for example, can be used to prepare the solution at the base of the active layer.

A surfactant can be added to the mounting phase to improve the solubility of the active principle or to stabilize the mounting suspension. The surfactant is used in a proportion from 0% to 50%, preferentially from 0% to 20%. Surfactants that can be used include fatty-acid alkaline or alkaline-earth salts, sodium dodecyl sulfate and docusate sodium being preferred; polyoxyethylenated oils, preferably polyoxyethylene hydrogenated castor oil; polyoxyethylene-polyoxypropylene copolymers; polyoxyethylene sorbitan esters; polyoxyethylene castor oil derivatives; stearates, preferably calcium, magnesium, aluminum or zinc stearates; polysorbates; stearyl fumarates, preferably sodium stearyl fumarate; glycerol behenate; benzalkonium chloride; acetyl-trimethylammonium bromide; cetyl alcohol and mixtures thereof.

To the degree possible, it is preferable to use solvents that are nontoxic and that can be easily eliminated by evaporation during drying so that no traces of the solvent remain in the microgranules.

The coating that enables controlled release contains a hydrophobic polymer that prevents the immediate release of the active principle in a quantity between 50% and 100%, preferably between 70% and 100%, of the dry weight of the aforesaid coating layer.

The coating ratio represents the ratio of the quantity of dry weight constituting the coating that ensures sustained release of the active principle to the total weight of the microgranule before coating (in dry weight). The coating ratio is from 0.1% to 50% w/w, preferably from 2% to 30% w/w, and more preferentially still from 5% to 30% w/w. In other words, the ratio between the weight of the dry varnish (=polymer and optional additives in dry weight) constituting the coating that prevents immediate release of the active principle and the total weight of the microgranule before coating (in dry weight) is comprised between 0.1% to 50% w/w, preferably from 2% to 30% w/w, and more preferably still from 5% to 30% w/w.

The polymers used to ensure sustained release of the active principle are hydrophobic polymers, preferably, selected from the group comprising non-water-soluble cellulose derivatives, (meth)acrylic (co)polymer derivatives, polyvinyl acetate derivatives and mixtures thereof.

More preferably, the hydrophobic polymer(s) that prevent the immediate release of the active principle is (are) selected from the following group: ethylcellulose, cellulose acetate butyrate, cellulose acetate, type A and type B ammoniomethacrylate copolymers sold under the brand name Eudragit®, in particular Eudragit® RS 30D, Eudragit NE 30D, Eudragit® RL 30D, Eudragit® RS PO and Eudragit® RL PO of the family of poly(ethyl acrylate, methyl methacrylate, trimethylamonioethyl methacrylate), polyvinyl acetates and mixtures thereof.

When the coating is prepared by aqueous route, a plasticizer can be added to the coating dispersion in a proportion from 0% to 50% w/w, preferably from 2% to 25% w/w, in dry weight of the polymer coating.

The plasticizer is selected in particular from the group comprising glycerol and esters thereof, preferably in the following sub-group: medium-chain triglycerides, acetylated glycerides, glyceryl monostearate, glyceryl triacetate, glyceryl tributyrate; phthalates, preferably in the following sub-group: dibutyl phthalate, diethyl phthalate, dimethyl phthalate, dioctyl phthalate; citrates, preferably in the following sub-group: acetyl tributyl citrate, acetyl triethyl citrate, tributyl citrate, triethyl citrate; sebacates, preferably in the following sub-group: diethyl sebacate, dibutyl sebacate; adipates; azelates; benzoates; chlorobutanol; polyethylene glycols; vegetable oils; fumarates, preferably diethyl fumarate; malates, preferably diethyl malate; oxalates, preferably diethyl oxalate; succinates, preferably dibutyl succinate; butyrates; cetyl alcohol esters; malonates, preferably diethyl malonate; castor oil (which is particularly preferred) and mixtures thereof.

More preferably, the plasticizer is selected from the group comprising acetylated monoglycerides, in particular Myvacet® 9-45, triethyl citrate (TEC), dibutyl sebacate, triacetin and mixtures thereof.

The surfactant is optionally present in the coating in a proportion from 0% to 30% w/w, preferably from 0% to 20% w/w, and more preferably still from 5% to 15% of the dry weight of the plasticizer. The surfactant is preferably selected from the group comprising fatty-acid alkaline or alkaline-earth salts, sodium dodecyl sulfate and docusate sodium being preferred; polyoxyethylenated oils, preferably polyoxyethylene hydrogenated castor oil; polyoxyethylene-polyoxypropylene copolymers; polyoxyethylene sorbitan esters; polyoxyethylene castor oil derivatives; stearates, preferably calcium, magnesium, aluminum or zinc stearates; polysorbates; stearyl fumarates, preferably sodium stearyl fumarate; glycerol behenate; benzalkonium chloride; acetyl-trimethylammonium bromide; cetyl alcohol and mixtures thereof.

An inert load can be present in the coating in a proportion from 0% to 50% w/w, preferably from 0% to 20% w/w, and more preferentially still from 5% to 20% of the dry weight of the polymer coating.

The inert load uniformly distributed in the coating is selected from the group comprising in particular talc, anhydrous colloidal silica, magnesium stearate, glycerol monostearate and mixtures thereof.

The phenomenon of resistance to immediate release of the active principle observed by the Applicant in an acid-alcohol medium shows a dependence according to the nature of the neutral used and the coating ratio of the microgranules.

Active Principle

The active layer of the inventive microgranules comprises at least one pharmaceutical active principle which can be of any nature.

The microgranules of the present invention can comprise as active principle, hormones or derivatives thereof, for example, active principles that act on the central nervous system, active principles that act on the cardiovascular system, antibiotics, antivirals and analgesics.

Active principles that act on the central nervous system are preferably selected from antiepileptics, antiparkinsonians, psychostimulants, psychotropics, antidepressants, anxiolytics and antipsychotics, for example.

Active principles that act on the cardiovascular system are preferably chosen from antihypertensives, antithrombotics, antiaggregants and cholesterol-lowering agents, in particular.

Antibiotics can be selected from beta-lactams, cyclines, aminoglycosides, macrolides, quinolones, glycopeptide antibiotics, imidazoles, sulfonamides, antitubercular drugs and anti-leprosy drugs, in particular.

Antivirals can be chosen in particular from replication inhibiters or viral multiplication inhibiters.

Analgesics can be chosen from non-opiate, weak opiate, mixed opioid, morphine or spasmodic analgesics, in particular hydrocodone, hydromorphone, morphine, oxycodone, oxymorphone, tramadol, gabapentin and derivatives thereof.

Method for Preparing Microgranules

The present invention further relates to the method for preparing microgranules previously described which comprises the following steps:

the introduction of spherical neutral carriers that are insoluble or rendered insoluble into a fluidized bed reactor, the spraying on these spherical neutral carriers of at least one active principle in solution or in suspension in an organic and/or aqueous solvent supplemented with at least one water-soluble or non-water-soluble polymer (binder), the spraying of a coating suspension comprising at least one hydrophobic polymer on the coated particles obtained in the preceding step, optionally, the drying of the medicinal microgranules thus obtained.

Preparation of the Mounting Dispersion

The active-layer mounting step of the present invention makes it possible to obtain microgranules whose content in active principle is both precise and uniform.

The mounting dispersion is the dispersion in which the active principles will be dissolved or suspended (dispersed) and which will be sprayed on the surface of the microgranules. This dispersion advantageously contains a conventional binder which is also dissolved.

Mounting of the Active Layer

The active principle is applied to the granules in a conventional way by spraying, in a fluidized bed reactor or perforated turbine, for example. Generally, this process rests on the simultaneous spraying through a nozzle of the active principles and optionally a binder which are dissolved or dispersed in the mounting solution, which guarantees for this step of the method a perfect homogeneity of content.

The necessary time for mounting is highly variable and depends on the quantity of active principle to be sprayed and its solubility in the mounting solution. Generally it is between 1 hour and 10 hours.

At the end of the mounting step, the microgranules are dried in a fluidized bed reactor or perforated turbine and then sieved.

Microgranule Coating

The coating polymer is applied to the preceding microgranules in a conventional way by spraying, in a fluidized bed reactor or perforated turbine, for example. Generally, this method rests on the simultaneous spraying through a nozzle of the coating polymers and optionally a plasticizer and/or a surfactant and/or an inert load which are dissolved or dispersed in a suitable solvent.

An organic solution of polymer can be used for the coating: in this case, the method consists of spraying of the solution and drying in the same apparatus.

If the excipient is water, an aqueous dispersion of polymer is used; a plasticizer must be added to improve the quality of the coating. The method thus consists of the spraying of the dispersion, drying in the same apparatus and, if necessary, a step of curing of the coating film which makes it possible to obtain a homogeneous and uniform film. Curing can take place in a fluidized bed reactor, perforated turbine or oven, for example.

The time necessary for coating is highly variable and depends on the quantity of polymer to be sprayed. Generally it is between 1 hour and 10 hours.

At the end of the coating step, the microgranules are dried in a fluidized bed reactor and then sieved.

Dissolution and Dosage Tests

Generally, the dosage and dissolution conditions of the microgranules in line with the invention are those prescribed by the various Pharmacopoeias, in particular European, American or Japanese.

Thus, to determine the release kinetics of the various systems studied, a conventional temperature-controlled paddle or basket dissolution apparatus can be used. The medicinal units are introduced into each flask and samples are taken periodically to determine the quantity of active principle released over time. Samples can be taken manually or automatically and analyses can be carried out directly with a UV/visible spectrophotometer or after HPLC (high-performance liquid chromatography) separation coupled with UV/visible detection, for example.

The invention further relates to the use of an oral pharmaceutical form containing sustained-release microgranules comprising a neutral carrier that is insoluble in water or in an alcohol solution, or a neutral rendered insoluble in water or in an alcohol solution, comprising at least one mounting layer comprising at least one active principle and optionally a binder; the whole comprising at least a second coating containing at least one hydrophobic polymer that prevents the immediate release of the active principle, wherein the aforementioned pharmaceutical form is intended to avoid or limit the immediate release of the active principle induced by the consumption of alcohol during the administration of said pharmaceutical form.

EXAMPLES

Example 1

Alcohol-Resistant Sustained-Release Diltiazem HCl Microgranules (10% Coating Ratio)

a) Preparation of Sustained-Release Diltiazem HCl Microgranules

The active principle used is diltiazem hydrochloride (Zambon) of formula $C_{22}H_{26}N_2O_4S$, HCl.

The neutral cores used are sugar spheres (Suglets® 30 NPPharm) and cellulose spheres (Ethispheres® 600 NPPharm). The size of these carriers is about 500 µm to 700 µm.

The binder used is polyvinylpyrrolidone (PVP K-30, BASF). It is solubilized in water and then diltiazem HCl is added to this aqueous solution, constituting the mounting solution.

The composition of the mounting solution and the quantities of materials used for the mounting step are as follows:

|  | Quantity (grams) | | Composition |
| --- | --- | --- | --- |
|  | Sugar neutrals | Cellulose neutrals | in dry weight (%) |
| Neutral cores | 800 | 1500 | 78 |
| PVP K-30 | 25 | 47 | 2 |
| Diltiazem HCl | 200 | 375 | 20 |
| Purified water | 800 | 1500 | N/A |
| Total in dry weight | 1025 | 1922 | 100 |

N/A: Not applicable

The cores are introduced into a fluidized bed reactor (Ohlmann) equipped with a Wurster coater. The mounting solution is bottom-sprayed from a 1.2 mm diameter nozzle. After the mounting step, the particles are sieved with 500 µm and 900 µm meshes in order to eliminate partial and double particles, respectively.

The coating suspension is prepared from a commercial preparation of Aquacoat® ECD 30 (FMC) which is an aqueous dispersion containing 29% to 32% dry matter including 24.5% to 29.5% ethylcellulose, 0.9% to 1.7% sodium lauryl sulfate and 1.7% to 3.3% cetyl alcohol. A plasticizer, triethyl citrate (Vertellus), is added to this suspension. The suspension is then diluted in order to obtain an aqueous dispersion with 15% dry weight.

The composition of the final coating suspension is as follows:

|  | Composition (%) | Composition in dry weight (%) |
|---|---|---|
| Aquacoat ® ECD 30 (dry weight) | 40.3 (12.09) | 15 |
| Triethyl citrate | 2.9 |  |
| Purified water | 56.8 | N/A |

The coating suspension is sprayed on the microgranules mounted with diltiazem HCl.

The quantities of the materials used for the coating step are as follows:

|  | Quantity (grams) to obtain a 10% coating ratio |
|---|---|
| Cores mounted with diltiazem HCl | 900 |
| Coating suspension with 15% dry weight (dry weight) | 600 (90) |
| Total in dry weight | 990 |

Coating is carried out in a fluid bed reactor (OHLMANN) equipped with a Wurster coater. The coating is bottom-sprayed from a 1.2 mm diameter nozzle. After the coating step, the particles are sieved with 500 μm and 1000 μm meshes in order to eliminate partial and double particles, respectively.

The coating film is cured in an oven (Firlabo) for 24 h at 60° C. with 75% relative humidity (RH).

The qualitative and quantitative compositions of the diltiazem HCl microgranules are summarized in the following table.

|  |  | Composition (%) to obtain a 10% coating ratio |
|---|---|---|
| Mounting | Neutral carrier | 70.6 |
|  | PVP K-30 | 2.2 |
|  | Diltiazem HCl | 17.6 |
| Coating | Aquacoat ® ECD 30 (in dry weight) | 7.3 |
|  | Triethyl citrate | 1.8 |
| Lubrication | Aerosil ® R972 | 0.5 | b) Microgranule Dosage and Dissolution

Tests of release of the active principle in vitro are carried out in a revolving-paddle dissolution apparatus (European Pharmacopoeia, Sotax AT7, IDIS software). The analysis is carried out with a UV/visible spectrophotometer (Kontron Instruments spectrophotometer, Uvikon 922) at a wavelength of 237 nm.

The samples are stirred constantly in flasks each containing 900 ml of dissolution medium and the temperature is kept constant at 37° C. (±0.5° C.). The dissolution media used are comprised either of 0.1 N HCl or of a 0.1 N HCl/absolute ethanol mixture with an absolute ethanol concentration of 10% or 20% (v/v). The paddles rotate at 100 rpm.

Samples are taken continuously over 24 h in each of the six flasks of the apparatus. For each batch, the test is carried out on three flasks, with three microgranule test samples each equivalent to 150 mg of active principle.

c) Profiles Obtained as a Function of the Two Types of Carriers

Figure 1:
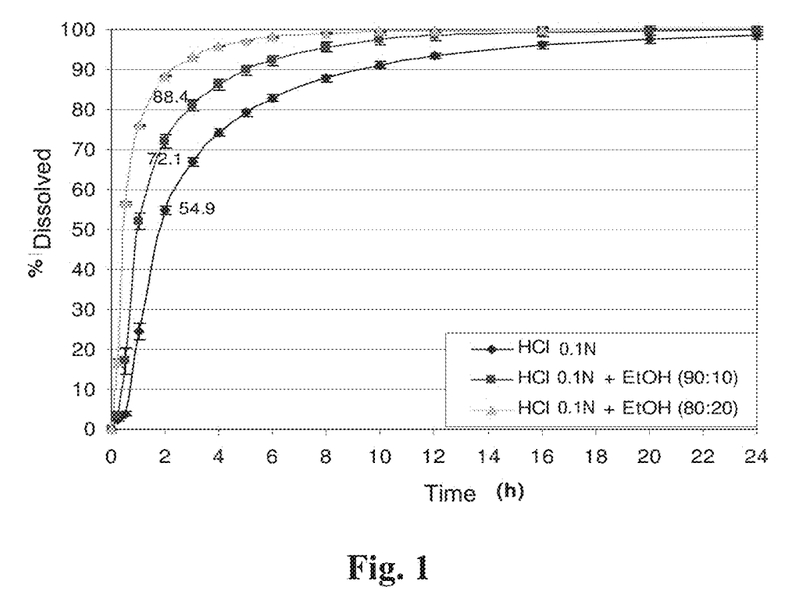
FIG. 1: Dissolution profiles of diltiazem HCl from sugar neutrals coated with ethylcellulose+TEC (10% coating ratio) in various media.
Figure 2:
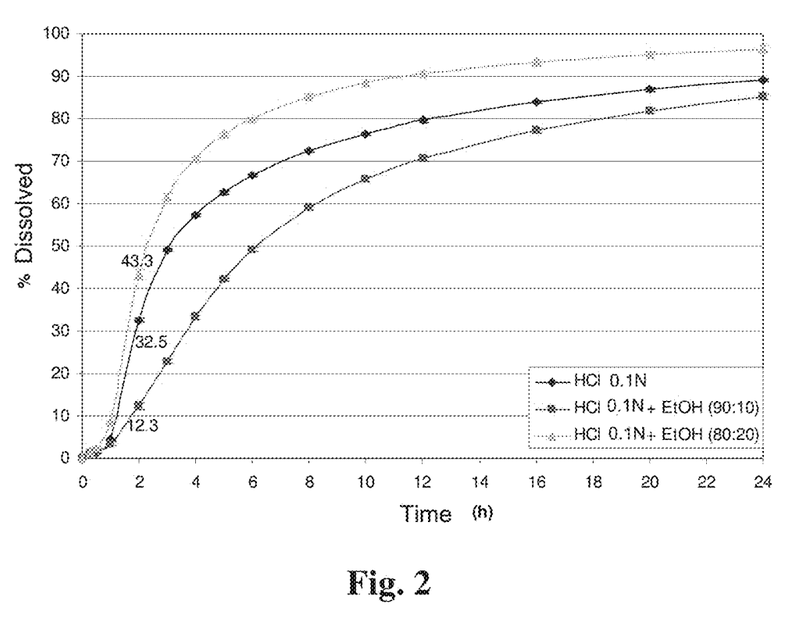
FIG. 2: Dissolution profiles of diltiazem HCl from cellulose neutrals coated with ethylcellulose+TEC (10% coating ratio) in various media.

The dissolution profiles obtained in 0.1 N HCl and in mixtures of 0.1 N HCl and 10% and 20% (v/v) absolute ethanol of microgranules with a 10% coating ratio are presented in FIGS. 1 and 2.

FIG. 1 shows that the rate of release of diltiazem HCl mounted on sugar carriers increases with an increase in ethanol concentration compared to the medium comprised of 0.1 N HCl alone. The profile obtained in the presence of 20% (v/v) alcohol is an immediate-release profile. There is thus loss of the sustained-release effect in the presence of alcohol for this formulation of sustained-release microgranules. Conversely, the systems containing cellulose neutrals indeed exhibit sustained release in media with ethanol concentrations of 0%, 10% and 20% (v/v).

Variation in the percentages of diltiazem HCl released in acid-alcohol media or in 0.1 N HCl for each system studied can be calculated. The following table presents these variations at the 2 h time point, which is most representative of resistance to alcohol based on the gastrointestinal absorption rate of ethanol ($C_{max} \leq 2$ h), according to the collective expertise of INSERM (2001).

|  |  | 10% ethanol (%) | 20% ethanol (%) |
|---|---|---|---|
| Sugar neutrals | Variation at t (2 h) | 17 | 34 |
| Cellulose neutrals | Variation at t (2 h) | −20 | 11 |

For systems containing sugar neutrals, all the variations are greater than 15%. On the other hand, the variations observed with systems containing cellulose neutrals are less than 15% for the two ethanol concentrations. The cellulose carrier system thus seems to have greater potential for the development of alcohol-resistant sustained-release forms than the sugar carrier system.

Example 2

Alcohol-Resistant Sustained-Release Diltiazem HCl Microgranules (20% Coating Ratio)

According to a variant of Example 1, alcohol-resistant diltiazem HCl microgranules can be obtained by preparing a 20% coating ratio.

The preparation, dosage and dissolution methods for the microgranules remain identical to Example 1, except for their quantitative composition which is summarized in the following table:

|  |  | Composition (%) to obtain a 20% coating ratio |
|---|---|---|
| Mounting | Cellulose neutral carrier | 64.7 |
|  | PVP K-30 | 2.0 |
|  | Diltiazem HCl | 16.2 |

-continued

|  |  | Composition (%) to obtain a 20% coating ratio |
|---|---|---|
| Coating | Aquacoat ® ECD 30 (in dry weight) | 13.4 |
|  | Triethyl citrate | 3.2 |
| Lubrication | Aerosil ® R972 | 0.5 |

Figure 3:
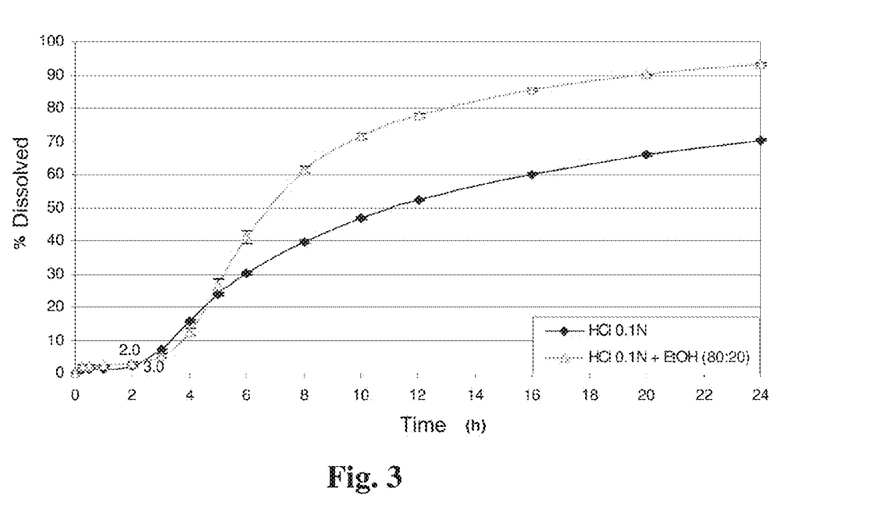
FIG. 3: Dissolution profiles of diltiazem HCl from cellulose neutrals coated with ethylcellulose+TEC (20% coating ratio) in various media.

The dissolution profiles obtained in 0.1 N HCl and in a mixture of 0.1 N HCl and 20% (v/v) absolute ethanol of microgranules with a 20% coating ratio are presented in FIG. 3.

The variation of the percentages of active principle released after 2 h in 0.1 N HCl compared to the acid-alcohol medium is 1%, which shows that these sustained-release microgranules are alcohol resistant.

Example 3

Diltiazem HCl Microgranules Incorporating an Agent D According to Patent WO 2007093642

According to a variant of Example 2, a pharmaceutically acceptable compound whose speed or capacity to hydrate or to solvate is higher in alcohol-free aqueous medium than in alcohol solution, described as "agent D" in document WO 2007093642, was incorporated in the microgranule formulation. According to the second embodiment of invention WO 2007093642, the agent D was incorporated in the coating, in a proportion of 10% of the total weight of said coating, as was described preferentially in said document.

The methods of preparation, dosage and dissolution of the microgranules remain identical to Example 1. The agent D is incorporated in the coating suspension containing the coating polymer and plasticizer. The quantitative composition of the microgranules is summarized in the following table:

|  |  | Composition (%) to obtain a 20% coating ratio |
|---|---|---|
| Mounting | Cellulose neutral carrier | 60.7 |
|  | PVP K-30 | 1.9 |
|  | Diltiazem HCl | 15.2 |
| Coating | Aquacoat ® ECD 30 (in dry weight) | 15.5 |
|  | Triethyl citrate | 3.9 |
|  | HPMC Pharmacoat ® 603 (agent D) | 2.3 |
| Lubrication | Aerosil ® R972 | 0.5 |

Figure 4:
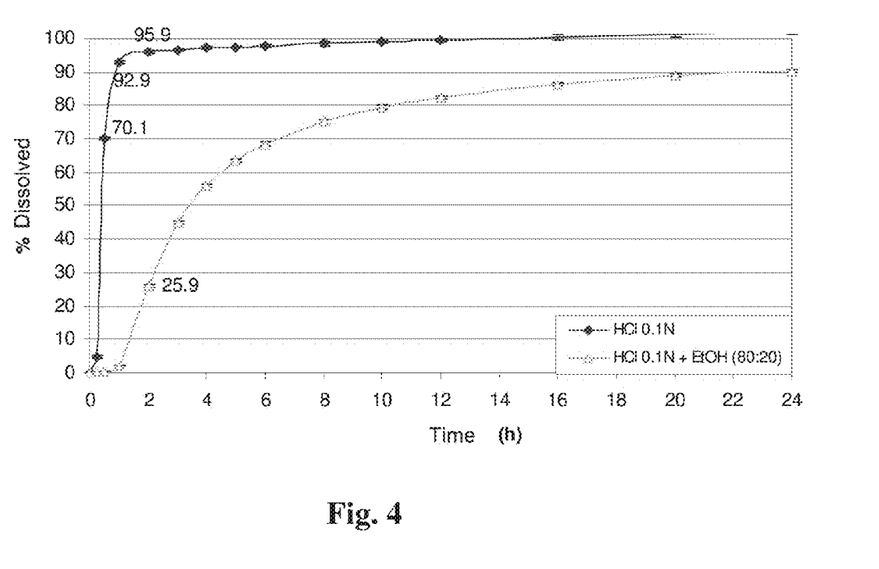
FIG. 4: Dissolution profiles of diltiazem HCl from microgranules prepared according to invention WO 2007093642 in various media (cellulose neutrals).

The dissolution profiles obtained in 0.1 N HCl and in a mixture of 0.1 N HCl and 20% (v/v) absolute ethanol of microgranules with a 20% coating ratio are presented in FIG. 4.

The percentage of active principle released in the ethanol-free medium reaches 70% at 30 min and then 93% at 1 h. These microgranules prepared according to invention WO 2007093642 thus do not constitute an alcohol-resistant sustained-release multiparticulate form.

Example 4

Alcohol-Resistant Sustained-Release Diltiazem HCl Microgranules Containing Sugar Neutrals Rendered Insoluble According to a variant of Example 1, showing that diltiazem HCl microgranules prepared from sugar neutrals are not alcohol resistant, alcohol-resistant diltiazem HCl microgranules can be obtained by rendering sugar neutrals insoluble in water or in an alcohol solution.

Sugar neutrals that are insoluble in water or in an alcohol solution are obtained by mounting a layer of excipients that are insoluble in water or in an alcohol solution on said neutrals. The composition of the mounting solution used and the quantities of the materials used are as follows:

|  | Quantity (grams) | Composition in dry weight (%) |
|---|---|---|
| Sugar neutrals | 700 | 72 |
| Aquacoat ® ECD 30 (dry weight) | 533 (160) | 16 |
| Triethyl citrate | 40 | 4 |
| Talc | 80 | 8 |
| Purified water | 1213 | N/A |
| Total in dry weight | 980 | 100 |

The sugar neutrals rendered insoluble in water or in an alcohol solution thus prepared are spherical and their diameter is increased by about 15% (diameter between 600 μm and 800 μm) compared to uncoated sugar neutrals.

Figure 5:
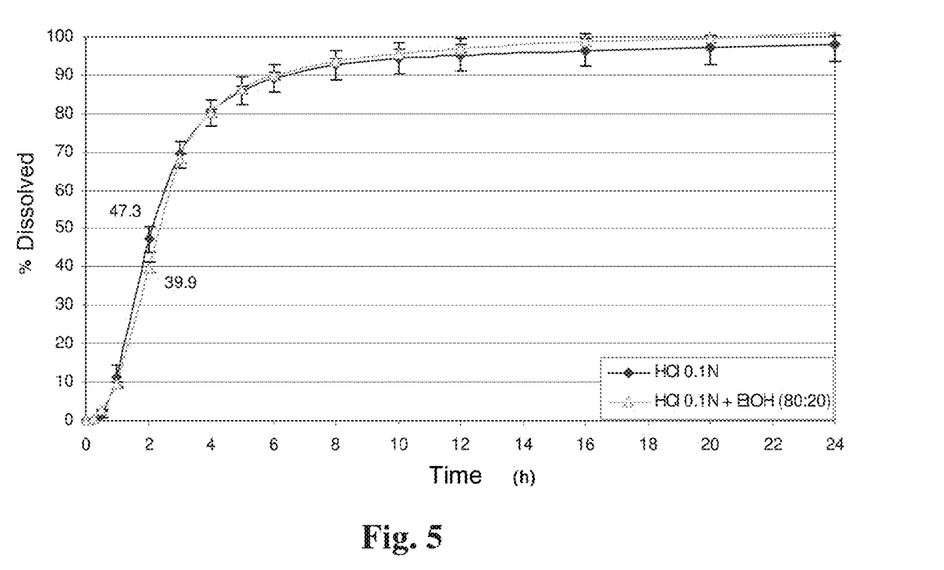
FIG. 5: Dissolution profiles of diltiazem HCl from sugar neutrals rendered insoluble and coated with ethylcellulose+TEC (20% coating ratio) in various media.

The insoluble neutrals are then used to prepare sustained-release diltiazem HCl microgranules. The methods of preparation, dosage and dissolution of said microgranules remain identical to Example 1, except for their quantitative composition which is summarized in the following table:

The dissolution profiles obtained in 0.1 N HCl and in a mixture of 0.1 N HCl and 20% (v/v) absolute ethanol of microgranules prepared with a 20% coating ratio are presented in FIG. 5.

Example 1 shows that microgranules prepared from sugar neutrals lose their property of sustained release in the presence of ethanol. FIG. 5 clearly shows that microgranules prepared from sugar neutrals rendered insoluble in water or in an alcohol solution retain their property of sustained release in the presence of alcohol. The variation in the percentage of active principle released after 2 h in 0.1 N HCl compared to the acid-alcohol medium is −7%, which shows that these sustained-release microgranules are alcohol resistant.

Example 5

Effect of Plasticizer on Alcohol-Resistant Sustained-Release Diltiazem HCl Microgranules

|  |  | Composition (%) to obtain a 20% coating ratio |
|---|---|---|
| Neutrals rendered insoluble | Sugar neutral support | 46.2 |
|  | Aquacoat ® ECD 30 (dry weight) | 10.6 |
|  | Triethyl citrate | 2.6 |
|  | Talc | 5.3 |

-continued

|  |  | Composition (%) to obtain a 20% coating ratio |
|---|---|---|
| Mounting | PVP K-30 | 2.0 |
|  | Diltiazem HCl | 16.2 |
| Coating | Aquacoat ® ECD 30 (dry weight) | 13.3 |
|  | Triethyl citrate | 3.3 |
| Lubrication | Aerosil ® R972 | 0.5 |

Use of Triacetin as Plasticizer:

According to a variant of Example 1, alcohol-resistant diltiazem HCl microgranules can be prepared using triacetin (Oleo Chemical) as a plasticizer in the coating suspension. Two coating ratios are presented: 15% and 20%.

The methods of preparation, dosage and dissolution of the microgranules remain identical to Example 1, except for their quantitative and qualitative compositions which are summarized in the following table:

|  |  | Composition (%) to obtain a 15% coating ratio | Composition (%) to obtain a 20% coating ratio |
|---|---|---|---|
| Mounting | Cellulose neutral carrier | 67.5 | 64.7 |
|  | PVP K-30 | 2.1 | 2.0 |
|  | Diltiazem HCl | 16.9 | 16.2 |
| Coating | Aquacoat ® ECD 30 (in dry weight) | 10.5 | 13.4 |
|  | Triacetin | 2.5 | 3.2 |
| Lubrication | Aerosil ® R972 | 0.5 | 0.5 |

Figure 6:
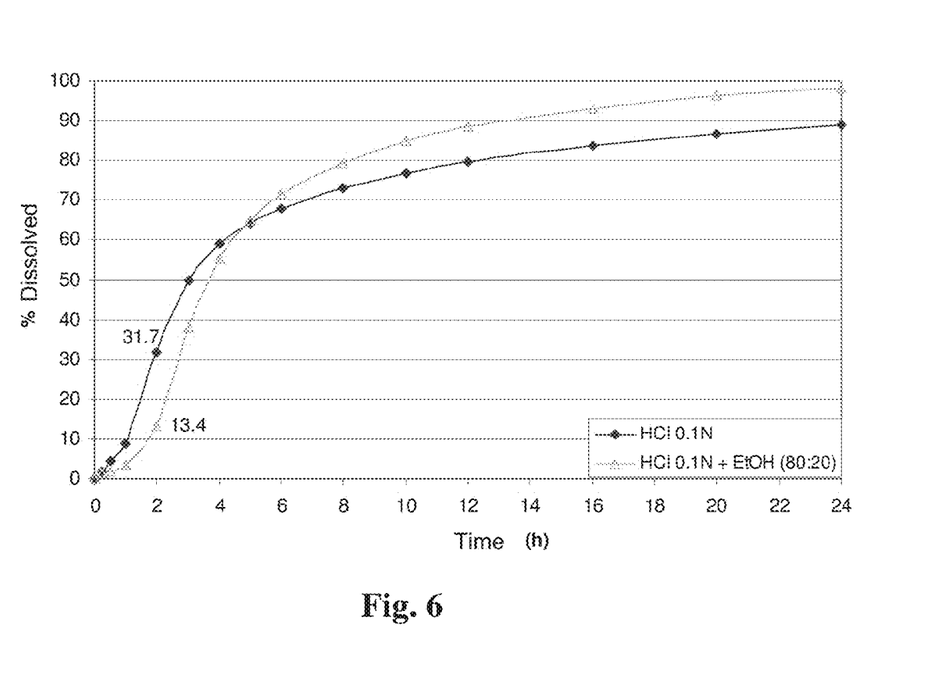
FIG. 6: Dissolution profiles of diltiazem HCl from cellulose neutrals coated with ethylcellulose+triacetin (20% coating ratio) in various media.

The dissolution profiles obtained in 0.1 N HCl and in a mixture of 0.1 N HCl and 20% (v/v) absolute ethanol of microgranules prepared with a 20% coating ratio are presented in FIG. 6.

Variation in the percentage of active principle released from these sustained-release microgranules after 2 h in 0.1 N HCl compared to the acid-alcohol medium is 2% and −18% for the 15% and 20% coating ratios, respectively.

Use of Acetylated Monoglycerides as Plasticizer:

According to a variant of Example 1, alcohol-resistant diltiazem HCl microgranules can be prepared using as plasticizers acetylated monoglycerides, in particular Myvacet® 9-45 (Kerry). In the present example, the coating ratio is 20%.

The methods of preparation, dosage and dissolution of the microgranules remain identical to Example 1, except for their quantitative and qualitative compositions which are summarized in the following table:

|  |  | Composition (%) to obtain a 20% coating ratio |
|---|---|---|
| Mounting | Cellulose neutral carrier | 64.7 |
|  | PVP K-30 | 2.0 |
|  | Diltiazem HCl | 16.2 |
| Coating | Aquacoat ® ECD 30 (in dry weight) | 13.4 |
|  | Myvacet ® 9-45 | 3.2 |
| Lubrication | Aerosil ® R972 | 0.5 |

Figure 7:
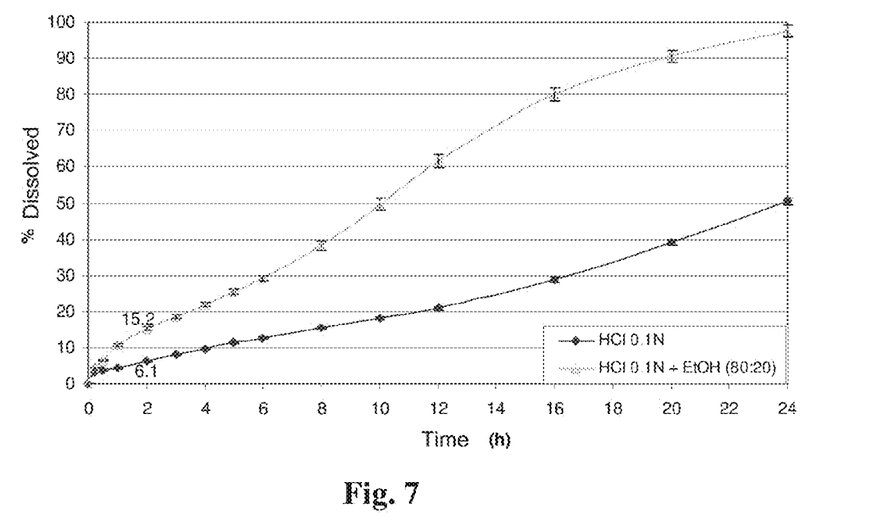
FIG. 7: Dissolution profiles of diltiazem HCl from cellulose neutrals coated with ethylcellulose+Myvacet 9-45 (20% coating ratio) in various media.

The dissolution profiles obtained in 0.1 N HCl and in a mixture of 0.1 N HCl and 20% (v/v) absolute ethanol for these microgranules are presented in FIG. 7.

Variation in the percentage of active principle released after 2 h in 0.1 N HCl compared to the acid-alcohol medium is 9%, which shows that these sustained-release microgranules are alcohol resistant.

Use of Dibutyl Sebacate as Plasticizer:

According to a variant of Example 1, alcohol-resistant diltiazem HCl microgranules can be prepared using dibutyl sebacate as plasticizer in the coating suspension. The coating ratio presented is 20%.

The methods of preparation, dosage and dissolution of the microgranules remain identical to Example 1, except for their quantitative and qualitative compositions which are summarized in the following table:

|  |  | Composition (%) to obtain a 20% coating ratio |
|---|---|---|
| Mounting | Cellulose neutral carrier | 64.7 |
|  | PVP K-30 | 2.0 |
|  | Diltiazem HCl | 16.2 |
| Coating | Aquacoat ® ECD 30 (in dry weight) | 13.4 |
|  | Dibutyl sebacate | 3.2 |
| Lubrication | Aerosil ® R972 | 0.5 |

Figure 8:
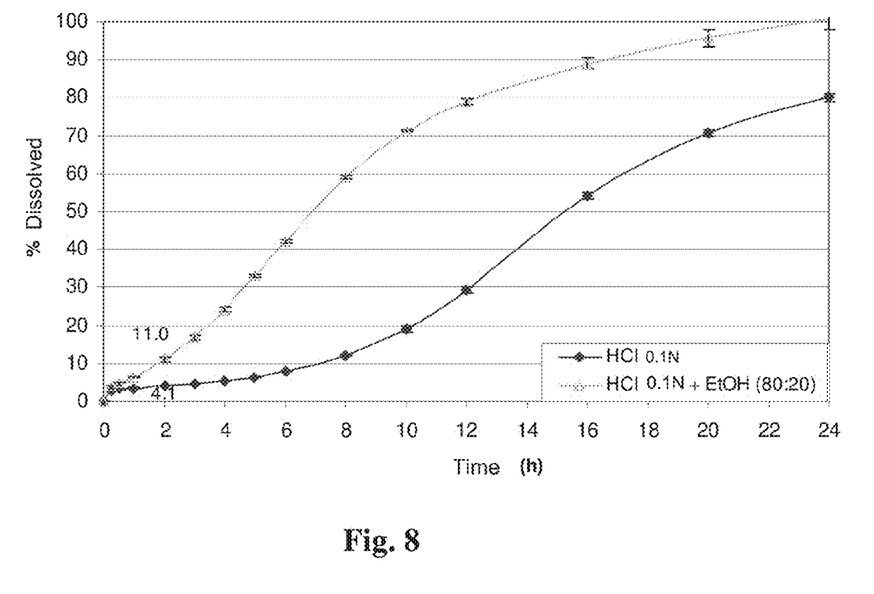
FIG. 8: Dissolution profiles of diltiazem HCl from cellulose neutrals coated with ethylcellulose+DBS (20% coating ratio) in various media.

The dissolution profiles obtained in 0.1 N HCl and in a mixture of 0.1 N HCl and 20% (v/v) absolute ethanol for these microgranules are presented in FIG. 8.

Variation in the percentage of active principle released after 2 h in 0.1 N HCl compared to the acid-alcohol medium is 7%, which shows that these sustained-release microgranules are alcohol resistant.

Example 6

Alcohol-Resistant Sustained-Release Carvedilol Phosphate Microgranules a) Preparation of Sustained-Release Carvedilol Phosphate Microgranules The active principle used is carvedilol phosphate hemihydrate (Zambon) of formula $C_{24}H_{26}N_2O_4 \cdot H_3PO_4 \cdot \frac{1}{2}H_2O$. The neutral cores used are sugar spheres (Suglets® 30 NPPharm) and cellulose spheres (Ethispheres® 600 NPPharm). The size of these carriers is on the order of 500 μm to 700 μm. The binder used is polyvinylpyrrolidone (PVP K-30, BASF) and several surfactants are used to stabilize the mounting suspension: simethicone (30% emulsion, Dow Corning) and polysorbate 80 (Seppic).

The composition of the mounting suspension and the quantities of the materials used for the mounting step are as follows:

|  | Quantity (grams) | | Composition in dry matter (%) | |
|---|---|---|---|---|
|  | Sugar neutrals | Cellulose neutrals | Sugar neutrals | Cellulose neutrals |
| Neutral cores | 1000 | 1000 | 68.2 | 62.8 |
| PVP K-30 | 150 | 240 | 10.2 | 15.1 |
| Polysorbate 80 | 15 | 32 | 1.0 | 2.0 |

-continued

|  | Quantity (grams) | | Composition in dry matter (%) | |
| --- | --- | --- | --- | --- |
|  | Sugar neutrals | Cellulose neutrals | Sugar neutrals | Cellulose neutrals |
| Simethicone (30% emulsion) | 1 | 1 | 0.02 | 0.02 |
| (dry weight) | (0.3) | (0.3) |  |  |
| Carvedilol phosphate | 300 | 320 | 20.5 | 20.1 |
| Purified water | 1832 | 1943 | N/A | N/A |
| Total in dry weight | 1465.3 | 1592.3 | 100 | 100 |

N/A: Not applicable

The neutral cores are introduced into a fluidized bed reactor (GPCG1, Glatt) equipped with a Wurster coater. The mounting suspension is bottom-sprayed from a 1.2 mm nozzle.

After the mounting step, the particles are sieved with 500 µm and 900 µm meshes in order to eliminate partial and double particles, respectively.

The coating suspension is prepared from a commercial preparation of Aquacoat® ECD 30 (FMC) to which a plasticizer, triethyl citrate (TEC), is added. The suspension is then diluted in order to obtain an aqueous dispersion with 15% dry weight.

The composition of the final coating suspension is as follows:

|  | Composition (%) | Composition in dry weight (%) |
| --- | --- | --- |
| Aquacoat® ECD 30 (dry weight) | 40.3 (12.09) | 15 |
| Triethyl citrate | 2.9 |  |
| Purified water | 56.8 | N/A |

The coating suspension is sprayed on the microgranules mounted with carvedilol phosphate.

The quantities of the materials used for the coating step are as follows:

|  | Quantity (grams) to obtain a 5% coating ratio |
| --- | --- |
| Cores mounted with carvedilol phosphate | 750.0 |
| Coating suspension with 15% dry weight | 250.0 |
| Dry weight | 37.5 |
| Total in dry weight | 787.5 |

The fluidized bed reactor (GPCG1, Glatt) is equipped with a Wurster coater. The coating solution is bottom-sprayed from a 1.2 mm diameter nozzle. After the coating step, the particles are sieved with 500 µm and 1000 µm meshes in order to eliminate partial and double particles, respectively.

The coating film is cured in an oven (Firlabo) for 24 h at 60° C. with 75% relative humidity (RH).

The qualitative and quantitative compositions of the carvedilol microgranules are summarized in the following table:

|  |  | Composition (%) to obtain a 5% coating ratio | |
| --- | --- | --- | --- |
|  |  | Sugar neutrals | Cellulose neutrals |
| Mounting | Neutral carriers | 64.7 | 59.5 |
|  | PVP K-30 | 9.7 | 14.3 |
|  | Polysorbate 80 | 1.0 | 1.9 |
|  | Simethicone (dry weight) | 0.02 | 0.02 |
|  | Carvedilol phosphate | 19.4 | 19.0 |
| Coating | Aquacoat® ECD 30 (dry weight) | 3.8 | 3.8 |
|  | Triethyl citrate | 0.9 | 0.9 |
| Lubrication | Aerosil® R972 | 0.5 | 0.5 | b) Microgranule Dosage and Dissolution

Tests of release of the active principle in vitro are carried out in a revolving-paddle dissolution apparatus (European Pharmacopoeia, Sotax AT7, IDIS software). The analysis is carried out with a UV/visible spectrophotometer (Kontron Instruments spectrophotometer, Uvikon 922) at a wavelength of 241 nm.

The samples are stirred constantly in flasks each containing 900 ml of dissolution medium and the temperature is kept constant at 37° C. (±0.5° C.). The dissolution media used are comprised either of 0.1 N HCl or of a 0.1 N HCl/absolute ethanol mixture with an absolute ethanol concentration of 10% or 20% (v/v). The paddles rotate at 100 rpm.

Samples are taken continuously over 24 h in each of the six flasks of the apparatus. For each batch, the test is carried out on three flasks, with three microgranule test samples each equivalent to 80 mg of active principle.

Figure 9:
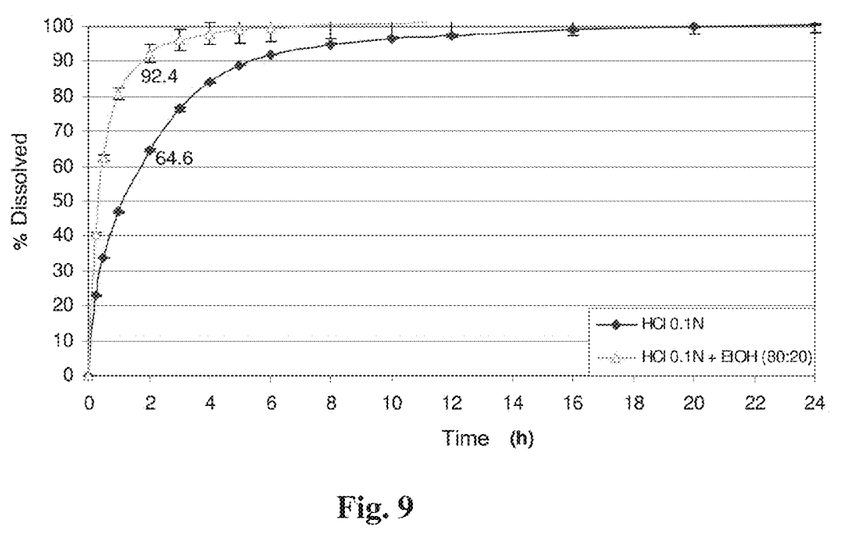
FIG. 9: Dissolution profiles of carvedilol phosphate from sugar neutrals coated with ethylcellulose+TEC (5% coating ratio) in various media.
Figure 10:
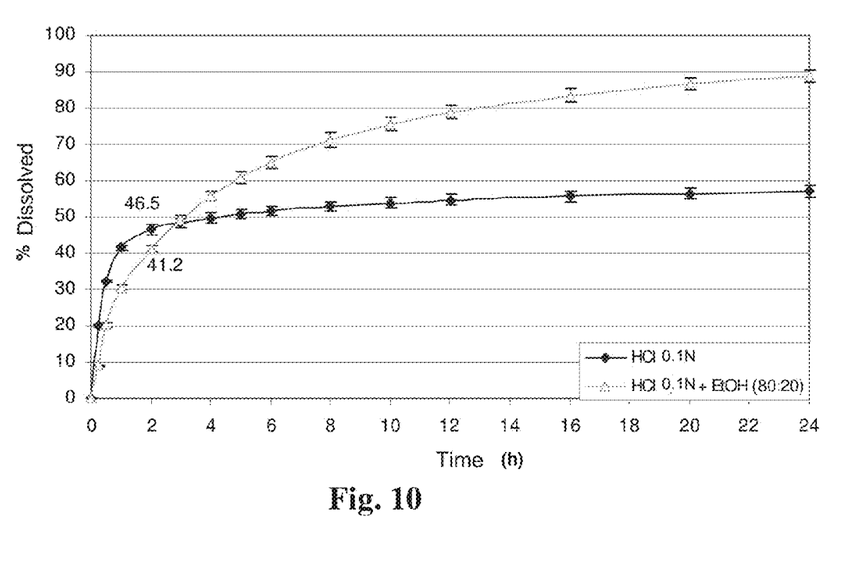
FIG. 10: Dissolution profiles of carvedilol phosphate from cellulose neutrals coated with ethylcellulose+TEC (5% coating ratio) in various media.

The dissolution profiles obtained in 0.1 N HCl and in the mixture of 0.1 N HCl and 20% (v/v) absolute ethanol for these microgranules are presented in FIGS. 9 and 10.

FIG. 9 shows that the rate of release of carvedilol phosphate mounted on sugar neutrals is much higher in the presence of ethanol compared to the medium comprised of 0.1 N HCl alone. The variation in the percentage of carvedilol phosphate released by these sustained-release microgranules after 2 h is 28%. These sustained-release microgranules are thus not alcohol resistant.

Conversely, the systems containing cellulose neutrals retain their property of sustained release of carvedilol phosphate in the presence of ethanol (FIG. 10). Variation in the percentage of carvedilol phosphate released by these sustained-release microgranules after 2 h in 0.1 N HCl compared to the acid-alcohol medium is −5%, which shows the resistance of this system to alcohol.

Example 7

Alcohol-Resistant Sustained-Release Carvedilol Phosphate Microgranules Prepared from Sugar Carriers Rendered Insoluble According to a variant of Example 6, showing that carvedilol phosphate microgranules prepared from sugar neutrals are not alcohol resistant, alcohol-resistant carvedilol phosphate microgranules can be obtained by rendering sugar neutrals insoluble in water or in an alcohol solution.

Sugar neutrals that are insoluble in water or in an alcohol solution are obtained by mounting a layer of excipients that are insoluble in water or in an alcohol solution on said neutrals. The composition of the mounting solution used and the quantities of the materials used are as follows:

|  | Quantity (grams) | Composition in dry weight (%) |
|---|---|---|
| Sugar neutrals | 700 | 72 |
| Aquacoat ® ECD 30 (dry weight) | 533 (160) | 16 |
| Triethyl citrate | 40 | 4 |
| Talc | 80 | 8 |
| Purified water | 1213 | N/A |
| Total in dry weight | 980 | 100 |

The sugar neutrals rendered insoluble in water or in an alcohol solution thus prepared are spherical and their diameter is increased by about 15% (diameter between 600 μm and 800 μm) compared to uncoated sugar neutrals.

The insoluble neutrals are then used to prepare sustained-release carvedilol phosphate microgranules. The methods of preparation, dosage and dissolution of said microgranules remain identical to Example 6, except for their quantitative composition which is summarized in the following table:

|  |  | Composition (%) to obtain a 5% coating ratio |
|---|---|---|
| Neutral coating | Sugar neutral carrier | 40.0 |
|  | Aquacoat ® ECD 30 (dry weight) | 9.2 |
|  | Triethyl citrate | 2.3 |
|  | Talc | 4.6 |
| Mounting | PVP K-30 | 12.5 |
|  | Polysorbate 80 | 1.3 |
|  | Simethicone (dry weight) | 0.02 |
|  | Carvedilol phosphate | 24.9 |
| Coating | Aquacoat ® ECD 30 (dry weight) | 3.8 |
|  | Triethyl citrate | 0.9 |
| Lubrication | Aerosil ® R972 | 0.5 |

Figure 11:
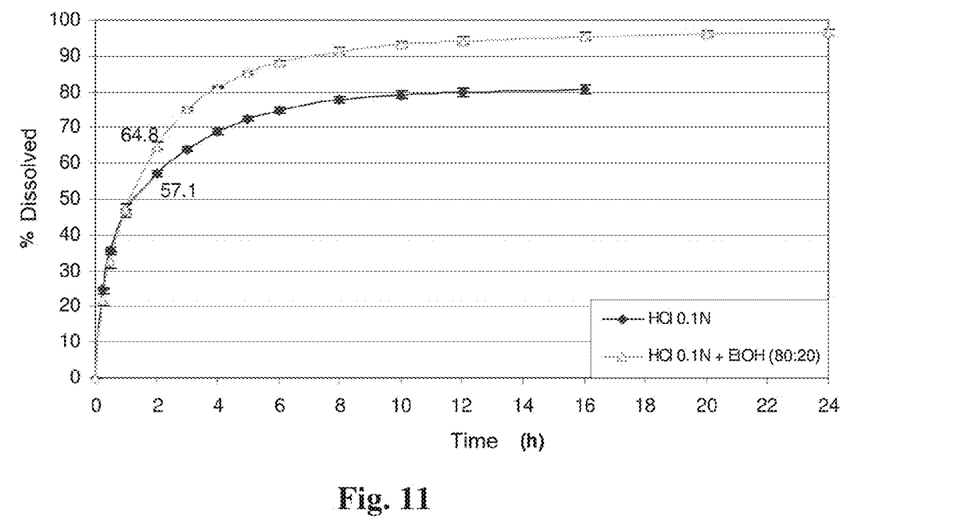
FIG. 11: Dissolution profiles of carvedilol phosphate from sugar neutrals rendered insoluble and coated with ethylcellulose+TEC (5% coating ratio) in various media.

The dissolution profiles obtained in 0.1 N HCl and in a mixture of 0.1 N HCl and 20% (v/v) absolute ethanol of microgranules prepared with a 20% coating ratio are presented in FIG. 11.

Example 6 shows that microgranules prepared from sugar neutrals lose their property of sustained release in the presence of ethanol. FIG. 11 clearly shows that microgranules prepared from sugar neutrals rendered insoluble in water or in an alcohol solution retain their property of sustained release in the presence of alcohol. The variation in the percentage of active principle released after 2 h in 0.1 N HCl compared to the acid-alcohol medium is 8%, which shows that these sustained-release microgranules are alcohol resistant.

Example 8

Alcohol-Resistant Sustained-Release Tolterodine Microgranules a) Preparation of Sustained-Release Tolterodine Tartrate Microgranules The neutral cores used are cellulose spheres (Celphere® 507, Asahi Kasei) whose size is on the order of 500 μm to 710 μm. The binder used is hypromellose 606 (Pharmacoat® 606, Shin-Etsu).

|  | Composition | |
|---|---|---|
|  | Composition in grams | Composition in percent |
| Celphere ® 507 | 744.0 | 96.62 |
| Tolterodine tartrate | 21.0 | 2.73 |
| Pharmacoat ® 606 | 5.0 | 0.65 |
| Purified water | 1400.0 | N/A |
| Total dry weight | 770.0 | 100.00 |

The neutral cores are introduced into a fluidized bed reactor (GPCG1, Glatt) equipped with a Wurster coater. The mounting suspension is bottom-sprayed from a 1.2 mm nozzle.

After the mounting step, the particles are sieved with 500 μm and 900 μm meshes in order to eliminate partial and double particles, respectively.

The coating suspension is prepared from a commercial preparation of Surelease® (Colorcon), which is a ready-to-use 25% ethylcellulose aqueous dispersion, preplasticized with medium-chain triglycerides, comprising stabilizers and co-stabilizers (oleic acid, ammonium hydroxide aqueous solution) and optionally an anti-adherent (colloidal silica).

The coating suspension is sprayed on the microgranules mounted with tolterodine. The quantities of the materials used for the coating step are as follows:

|  | Composition | |
|---|---|---|
|  | Composition in grams | Composition in percent |
| Neutrals mounted with tolterodine | 390.0 | 73.00 |
| Surelease ® (dry weight) | 480.84 (120.21) | 22.50 |
| Pharmacoat ® 606 | 24.04 | 4.50 |
| Purified water | 480.84 | N/A |
| Total dry weight | 534.25 | 100.00 |

The fluidized bed reactor (GPCG1, Glatt) is equipped with a Wurster coater. The coating is bottom-sprayed from a 1.2 mm nozzle. After the coating step, the particles are sieved with 500 μm and 1000 μm meshes in order to eliminate partial and double particles, respectively.

The coating film is cured in an oven for 4 h at 55° C.

The qualitative and quantitative compositions of the tolterodine microgranules are summarized in the following table.

|  | Relative composition (%) |
|---|---|
| Celphere ® 507 | 70.53 |
| Tolterodine tartrate | 2.00 |
| Pharmacoat ® 606 | 4.97 |
| Surelease ® (dry weight) | 22.50 |
| Total | 100.00 | b) Microgranule Dosage and Dissolution

Tests of release of the active principle in vitro are carried out in a basket dissolution apparatus (European Pharmacopoeia).

The samples are stirred constantly in flasks each containing 900 ml of dissolution medium and the temperature is kept constant at 37° C. (±0.5° C.). The dissolution media used are comprised either of a pH 6.8 medium or of a 0.1 N HCl/absolute ethanol mixture with an absolute ethanol concentration of 20% (v/v). The baskets rotate at 100 rpm.

Samples are taken during the first four hours of dissolution in each of the six flasks of the apparatus. For each batch, the test is carried out on three flasks, with three microgranule test samples each equivalent to 4 mg of active principle.

Figure 12:
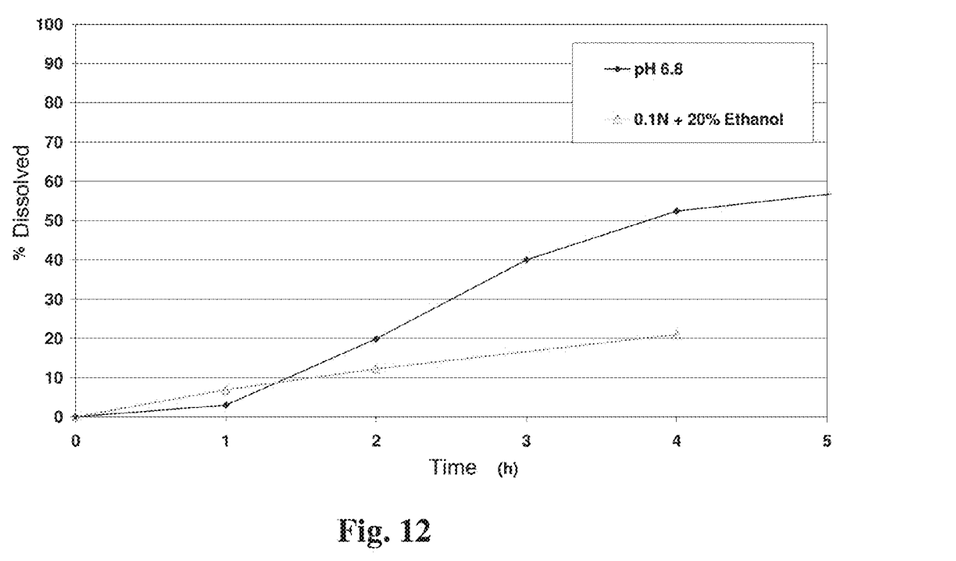
FIG. 12: Dissolution profiles of granules of tolterodine coated with Surelease+hypromellose in various media.

The dissolution profiles obtained in pH 6.8 medium and in a mixture of 0.1 N HCl and 20% (v/v) absolute ethanol for these microgranules are presented in FIG. 12.

Variation in the percentage of tolterodine released after 2 h in an aqueous medium and in the hydro-alcohol medium is −7.7%, indicating that this system is resistant to the presence of alcohol in the dissolution medium.

The invention claimed is:

1. A method for preventing or delaying release of an active principle from a pharmaceutical composition in the presence of alcohol with a concomitant consumption of alcohol, comprising:
   delivering the active principle in an oral pharmaceutical form containing sustained-release microgranules, wherein each of said microgranules comprises
   a. a neutral core rendered insoluble in water and in an alcohol solution, the neutral core consisting essentially of materials that are soluble in water and in an alcohol solution and being directly covered with one or more layers of material, each of which is selected from the group consisting of cellulose, microcrystalline cellulose, phosphate derivatives, silica and silicate derivatives, titanium dioxide, waxes, shellac, polyvinyl acetate and/or phthalate, and lactic and glycolic acid polymers;
   b. an active layer comprising the active principle and a pharmaceutically acceptable binder; and
   c. a coating layer comprising a hydrophobic polymer;
   wherein the percentage of active principle released after 2 h in an acid-alcohol medium of 0.1 N HCl containing alcohol and a quantity of ethanol between 4% and 30%, is not more than 15 points, 15% in absolute value, greater than that released in an acid medium of 0.1 N HCl; and the neutral carrier comprises a spherical or quasi spherical inert carrier of a size between 50 um and 3 mm.

2. The method according to claim 1, wherein the pharmaceutically acceptable binder is selected from the group consisting of cellulose derivatives, polyvinylpyrrolidone derivatives, polyethylene glycol derivatives, and mixtures thereof.

3. The method according to claim 1, further comprising at least one plasticizer in the coating.

4. The method according to claim 1, further comprising at least one surfactant in the active layer.

5. The method according to claim 1, wherein the hydrophobic polymer of the coating is selected from the group consisting of non-water-soluble cellulose derivatives, (meth) acrylic (co)polymer derivatives, polyvinyl acetate derivatives, and mixtures thereof.

6. The method according to claim 1, wherein the coating ratio is from 0.1% to 50% w/w.

7. The method according to claim 1, wherein the active principle is selected from hormones or derivatives thereof, active principles that act on the central nervous system, active principles that act on the cardiovascular system, antibiotics, antivirals, and analgesics.

8. The method according to claim 1, wherein the coating ratio is from 2% to 30% w/w.

9. The method according to claim 1, wherein the coating ratio is from 5% to 30% w/w.

* * * * *